United States Patent
Hadwen et al.

(10) Patent No.: US 9,539,573 B1
(45) Date of Patent: Jan. 10, 2017

(54) EWOD DEVICE WITH CALIBRATED SERIAL DILUTION FUNCTION

(71) Applicant: Sharp Kabushiki Kaisha, Osaka (JP)

(72) Inventors: Benjamin James Hadwen, Oxford (GB); Christopher James Brown, Oxford (GB); Julie Karen Deacon, Berks (GB)

(73) Assignee: Sharp Kabushiki Kaisha, Osaka (JP)

( * ) Notice: Subject to any disclaimer, the term of this patent is extended or adjusted under 35 U.S.C. 154(b) by 55 days.

(21) Appl. No.: 14/747,177

(22) Filed: Jun. 23, 2015

(51) Int. Cl.
  *B01L 3/00* (2006.01)
  *G01N 27/02* (2006.01)
  *G01N 27/22* (2006.01)
  *G01N 27/447* (2006.01)

(52) U.S. Cl.
  CPC ..... *B01L 3/50273* (2013.01); *G01N 27/44791* (2013.01); *B01L 2400/0421* (2013.01)

(58) Field of Classification Search
  CPC ............... B01L 3/50273; B01L 3/5027; B01L 2400/0421; B01L 2400/0427; G01N 27/44791; G01N 27/22; G01N 27/02
  See application file for complete search history.

(56) References Cited

U.S. PATENT DOCUMENTS

| | | | |
|---|---|---|---|
| 6,565,727 B1 | 5/2003 | Shenderov | |
| 6,911,132 B2 | 6/2005 | Pamula et al. | |
| 7,163,612 B2 | 1/2007 | Sterling et al. | |
| 7,439,014 B2 | 10/2008 | Pamula et al. | |
| 8,653,832 B2 | 2/2014 | Hadwen et al. | |
| 8,872,527 B2 | 10/2014 | Sturmer et al. | |
| 2010/0096266 A1 | 4/2010 | Kim et al. | |
| 2013/0115703 A1 | 5/2013 | Bhattacharya et al. | |
| 2013/0161193 A1* | 6/2013 | Jacobs | B01L 3/502792 204/604 |

FOREIGN PATENT DOCUMENTS

EP  2404675 A1  1/2012

OTHER PUBLICATIONS

Ren et al. "Automated on-chip droplet dispensing with volume control by electro-wetting actuation and capacitance metering", Sensors and Actuators B 98 (2004) 319-327.*

(Continued)

*Primary Examiner* — Susan D Leong
(74) *Attorney, Agent, or Firm* — Renner, Otto, Boisselle & Sklar, LLP

(57) ABSTRACT

In a method of performing dilution of a droplet in an EWOD device, a parent droplet is provided on an electrode array of the EWOD device, wherein the parent droplet has a first concentration of a species. A diluent droplet also is provided on the electrode array of the EWOD device. The method includes controlling actuation voltages applied to the electrode array of the EWOD device to join the parent droplet and the diluent droplet into a product droplet having a diluted second concentration of the species different from the first concentration in the parent droplet. The actuation voltages then are controlled to split the product droplet into one or more daughter droplets having the second concentration of the species. A dilution ratio may be calibrated based on the volumes of the droplets. Serial dilution steps may be performed to generate daughter droplets of different species concentrations at each step.

20 Claims, 11 Drawing Sheets

(56) References Cited

OTHER PUBLICATIONS

"Digital microfluidics: is a true lab-on-a-chip possible?", R.B. Fair, Microfluid Nanofluid (2007) 3:245-281).
"Programmable large area digital microfluidic array with integrated droplet sensing for bioassays", Hadwen et al, Lab Chip. Sep. 21, 2012;12(18):3305-13.
"Digital PCR hits its stride", Monya Baker, Nature methods vol. 9 No. 6 p. 541.

\* cited by examiner

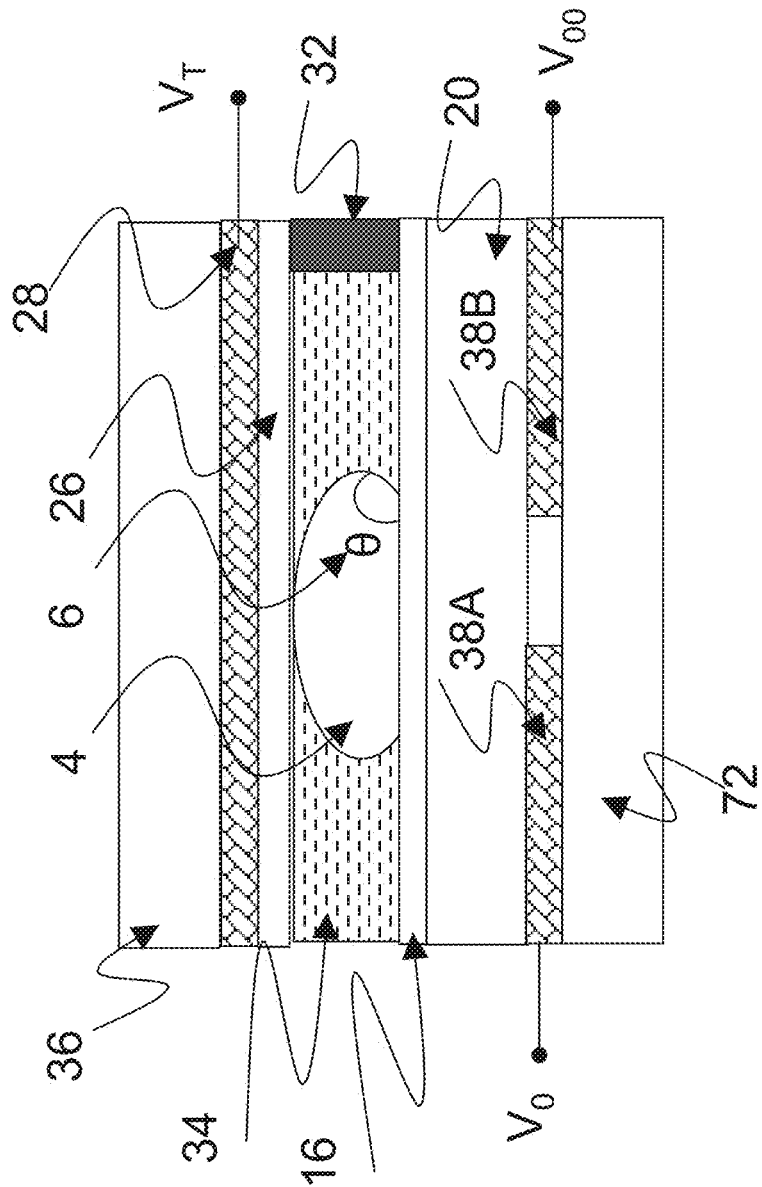
*Figure 1: PRIOR ART*

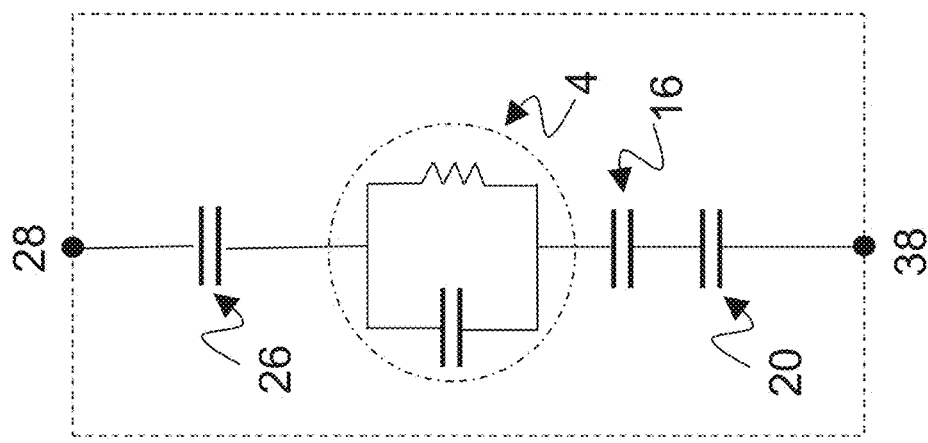
Figure 1B: prior art

EWOD DEVICE WITH CALIBRATED SERIAL DILUTION FUNCTION

TECHNICAL FIELD

The present invention relates to active matrix arrays and elements thereof, and particularly relates to digital microfluidics, and more specifically to Active Matrix Electro-wetting-On-Dielectric (AM-EWOD) devices and methods of driving such devices.

BACKGROUND ART

Electro-wetting on dielectric (EWOD) is a well known technique for manipulating droplets of fluid by application of an electric field. Active Matrix EWOD (AM-EWOD) refers to implementation of EWOD in an active matrix array incorporating transistors, for example by using thin film transistors (TFTs). EWOD (or AM-EWOD) is thus a candidate technology for digital microfluidics for lab-on-a-chip technology. An introduction to the basic principles of the technology can be found in "Digital microfluidics: is a true lab-on-a-chip possible?", R. B. Fair, Microfluid Nanofluid (2007) 3:245-281).

FIG. 1 shows a part of a conventional EWOD device in cross section. The device includes a lower substrate 72, the uppermost layer of which is formed from a conductive material which is patterned so that a plurality of electrodes 38 (e.g., 38A and 38B in FIG. 1) are realized. The electrode of a given array element may be termed the element electrode 38. The liquid droplet 4, including a polar material (which is commonly also aqueous and/or ionic), is constrained in a plane between the lower substrate 72 and a top substrate 36. A suitable gap between the two substrates may be realized by means of a spacer 32, and a non-polar fluid 34 (e.g. oil) may be used to occupy the volume not occupied by the liquid droplet 4. An insulator layer 20 disposed upon the lower substrate 72 separates the conductive element electrodes 38A, 38B from a first hydrophobic coating 16 upon which the liquid droplet 4 sits with a contact angle 6 represented by θ. The hydrophobic coating is formed from a hydrophobic material (commonly, but not necessarily, a fluoropolymer).

On the top substrate 36 is a second hydrophobic coating 26 with which the liquid droplet 4 may come into contact. Interposed between the top substrate 36 and the second hydrophobic coating 26 is a reference electrode 28.

The contact angle θ 6 is defined as shown in FIG. 1, and is determined by the balancing of the surface tension components between the solid-liquid ($\gamma_{SL}$), liquid-gas ($\gamma_{LG}$) and non-ionic fluid ($\gamma_{SG}$) interfaces, and in the case where no voltages are applied satisfies Young's law, the equation being given by:

$$\cos\theta = \frac{\gamma_{SG} - \gamma_{SL}}{\gamma_{LG}} \quad \text{(equation 1)}$$

In operation, voltages termed the EW drive voltages, (e.g. $V_T$, $V_0$ and $V_{00}$ in FIG. 1) may be externally applied to different electrodes (e.g. reference electrode 28, element electrodes 38A and 38B, respectively). The resulting electrical forces that are set up effectively control the hydrophobicity of the hydrophobic coating 16. By arranging for different EW drive voltages (e.g. $V_0$ and $V_{00}$) to be applied to different element electrodes (e.g. 38A and 38B), the liquid droplet 4 may be moved in the lateral plane between the two substrates 72 and 36.

FIG. 1B shows a circuit representation of the electrical load presented between the element electrode 38 and the reference electrode 28. The liquid droplet 4 can be modeled as a resistor and capacitor in parallel, the hydrophobic coatings 16 and 26 as capacitors and the insulator 16 as a capacitor. For the purposes of driving and sensing, the electrical load functions effectively as a capacitor whose value depends on whether a liquid droplet 4 is present or not a given element electrode 38.

U.S. Pat. No. 6,565,727 (Shenderov, issued May 20, 2003) discloses a passive matrix EWOD device for moving droplets through an array.

U.S. Pat. No. 6,911,132 (Pamula et al., issued Jun. 28, 2005) discloses a two dimensional EWOD array to control the position and movement of droplets in two dimensions.

U.S. Pat. No. 6,565,727 further discloses methods for other droplet operations including the splitting and merging of droplets, and the mixing together of droplets of different materials.

U.S. Pat. No. 7,163,612 (Sterling et al., issued Jan. 16, 2007) describes how TFT based thin film electronics may be used to control the addressing of voltage pulses to an EWOD array by using circuit arrangements very similar to those employed in AM display technologies.

The approach of U.S. Pat. No. 7,163,612 may be termed "Active Matrix Electro-wetting on Dielectric" (AM-EWOD). There are several advantages in using TFT based thin film electronics to control an EWOD array, namely:

Electronic driver circuits can be integrated onto the lower substrate 72.

TFT-based thin film electronics are well suited to the AM-EWOD application.

They are cheap to produce so that relatively large substrate areas can be produced at relatively low cost.

TFTs fabricated in standard processes can be designed to operate at much higher voltages than transistors fabricated in standard CMOS processes. This is significant since many EWOD technologies require EWOD actuation voltages in excess of 20V to be applied.

A disadvantage of U.S. Pat. No. 7,163,612 is that it does not disclose any circuit embodiments for realizing the TFT backplane of the AM-EWOD.

EP2404675 (Hadwen et al., published Jan. 11, 2012) describes array element circuits for an AM-EWOD device. Various methods are known for programming and applying an EWOD actuation voltage to the EWOD element electrode 38. The voltage write function described includes a memory element of standard means, for example, based on Dynamic RAM (DRAM) or Static RAM (SRAM) and input lines for programming the array element.

US Application US20100096266 (Kim et al., published Apr. 22, 2010) describes an EWOD device having a reservoir site that is configured to hold a quantity of liquid. Droplets are dispensed from the reservoir using control circuitry with a feedback mechanism. The control circuitry is configured to measure the fluid volume on the electrodes and independently adjust an applied voltage to increase/decrease the quantity of fluid.

U.S. Pat. No. 7,439,014 (Pamula et al., issued Oct. 21, 2008) describes a method for effecting serial dilution on an EWOD device by combining a droplet with a droplet of wash buffer and then splitting the resultant droplet into two parts.

US Application US20130115703 (Bhattacharya et al., published May 9, 2013) describes a method for producing fluids with desired concentration factors by sequences of mix/split steps on an EWOD device.

Various methods are known for detecting the position and size of one or more droplets on an EWOD device. US8872527 (Sturmer et al., issued Oct. 28, 2014) describes a method for capacitance detection on an EWOD droplet actuator.

US8653832 (Hadwen et al., issued Feb. 18, 2014) describes how an impedance (capacitance) sensing function can be incorporated into the array element of an AM-EWOD device. The sensor function may be utilized to measure the position of one or more droplets on the array. The sensor function may further be utilized to measure the size of droplets which may overlap one or more elements of the array. A method of determining droplet size from sensor data is described in "Programmable large area digital microfluidic array with integrated droplet sensing for bioassays", Hadwen et al, Lab Chip. 2012 Sep. 21; 12(18):3305-13.

Digital polymerase chain reaction (dPCR) is a method for measuring the quantity of a target nucleic acid sequence in a sample of interest. The basic method is described in the article "Digital PCR hits its stride", Nature methods Vol. 9 No. 6 p 541, and involves the sample being diluted and partitioned into hundreds or even millions of separate reaction chambers so that each contains one or no copies of the sequence of interest. By counting the number of 'positive' partitions (in which the sequence is detected) versus 'negative' partitions (in which it is not), one can determine exactly how many copies of a DNA molecule were in the original sample.

SUMMARY OF INVENTION

A method of performing calibrated dilution steps in droplets on a droplet microfluidic device includes some or all of the following steps:
1. Serial dilution of a parent droplet to produce one or more daughter droplets and calibrating the dilution ratio(s) by measuring the size or volume of the parent and diluent droplets participating in each dilution step.
2. Performing serial dilution to produce a set of reagent droplets of calibrated volumes and concentrations. The diluent droplets participate in assay steps to generate a standard curve, with calibrated volumes and concentrations being used in calculation of the fit to the standard curve.
3. Performing serial dilution of an input sample to produce diluted sample droplets having different concentrations. The diluted sample droplets are then manipulated so as to participate in bio-chemical tests (assays). The final overall result of the test is obtained by combining information comprised from one or more of the individual reactions having sample of different concentrations.
4. A method of performing digital-PCR in droplet format whereby:
  The sample is serially diluted to produce reaction droplets of different concentrations of the starting sample material.
  The diluted droplets are further divided into a multiplicity of smaller droplets of each concentration.
  The smaller droplets participate in a multiplicity of digital-PCR reactions at each concentration.
  The overall result of the digital-PCR is determined by combining information from the digital PCR reaction at each concentration.
5. Performing serial dilution of a droplet by repeated merge and split operations, such that each product droplet is dispensed from a common parent droplet held stationary (to minimize sample loss).

The advantages of the invention are that:
  The concentration of a reagent in a diluted droplet can be controlled very accurately.
  A series of droplets whose concentrations are in a precisely controlled ratio may be created.
  The accurate dilution of droplets facilitates the creation of an accurately defined standard curve. This will increase the accuracy of the assay overall.
  The accurate dilution of droplets may facilitate an accurate digital-PCR reaction that is capable of accurately detecting quantities of the target nucleic acid sequence, for samples having a nucleic acid concentration that may vary over several orders of magnitude, and such that the digital-PCR method requires only a relatively small number of droplets to be assayed.

BRIEF DESCRIPTION OF DRAWINGS

In the annexed drawings, like references indicate like parts or features:

FIG. 1 is a schematic diagram depicting a conventional EWOD device in cross-section;

FIG. 1B is a schematic diagram depicting the electrical load present between an element electrode and the reference electrode in the case where a liquid droplet is present at the element electrode;

Figure 2:
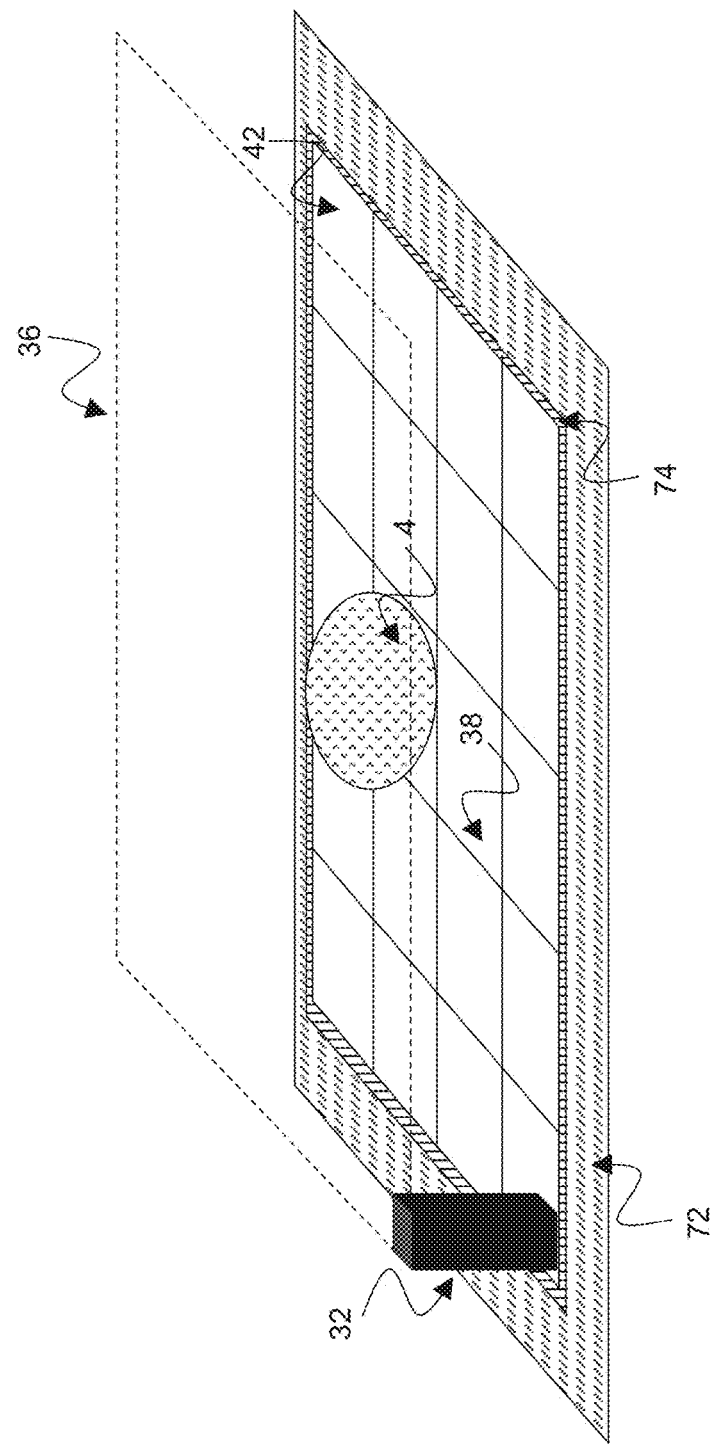
FIG. 2 is a schematic diagram depicting an AM-EWOD device in schematic perspective in accordance with a first and exemplary embodiment of the invention.

DESCRIPTION OF REFERENCE NUMERALS 4 liquid droplet
6 contact angle θ
16 First hydrophobic coating
20 Insulator layer
26 Second hydrophobic coating
28 Reference electrode
32 Spacer
34 Non-polar fluid
36 Top substrate
38/38A and 38B Array Element Electrodes
42 Electrode array 44 Capacitor
46 Actuation circuit
48 Sensor circuit
72 Lower Substrate
74 Thin film electronics
76 Row driver circuit
78 Column driver circuit
80 Serial interface
82 Connecting wires
83 Voltage supply interface
84 Array element circuit
86 Column detection circuit
88 Sensor row addressing
90 Data points from reaction droplets
92 Standard curve
94 Data point from sample droplet
96 Calculated concentration of sample droplet
98 Digital PCR
100 Digital PCR data

DETAILED DESCRIPTION OF INVENTION

FIG. 2 is a schematic diagram depicting an AM-EWOD device in accordance with an exemplary embodiment of the present invention. The AM-EWOD device has a lower substrate 72 with thin film electronics 74 disposed upon the lower substrate 72. The thin film electronics 74 are arranged to drive the array element electrodes 38. A plurality of array element electrodes 38 are arranged in an electrode array 42, having X by Y elements where X and Y may be any integer. A liquid droplet 4, which may include any polar liquid and which typically may be ionic and/or aqueous, is enclosed between the lower substrate 72 and a top substrate 36, although it will be appreciated that multiple liquid droplets 4 can be present. A suitable gap between the two substrates may be realized by means of a spacer 32, and a non-polar fluid 34, which could be oil, for example n-dodecane, silicone oil or other alkane oil, or alternatively air, may be used to occupy the volume not occupied by the liquid droplet 4.

Figure 3:
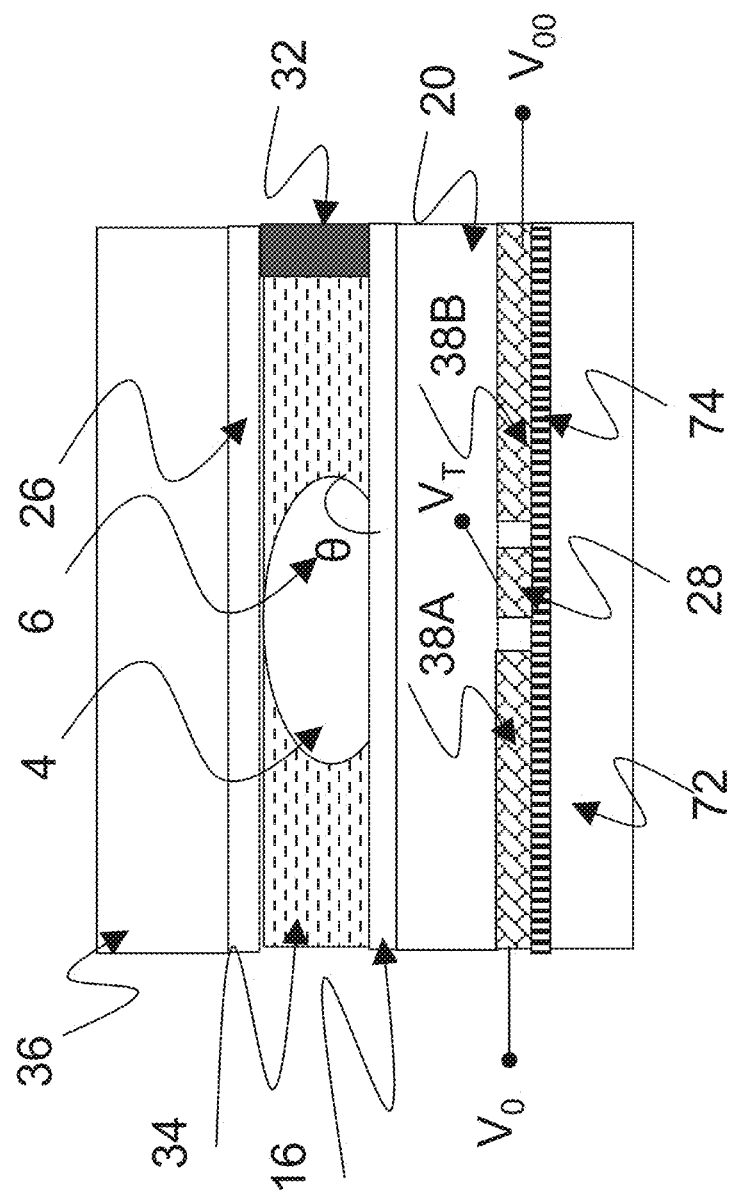
FIG. 3 shows a cross section through some of the array elements of the exemplary AM-EWOD device of FIG. 2.

FIG. 3 is a schematic diagram depicting a pair of the array elements 38A and 38B in cross section that may be utilized in the AM-EWOD device of FIG. 2. The device configurations of FIGS. 2 and 3 bear similarities to the conventional configuration shown in FIG. 1, with the AM-EWOD device of FIGS. 2 and 3 further incorporating the thin-film electronics 74 disposed on the lower substrate 72. The uppermost layer of the lower substrate 72 (which may be considered a part of the thin film electronics layer 74) is patterned so that a plurality of the array element electrodes 38 (e.g., 38A and 38B in FIG. 3) are realized. These may be termed the array element electrodes 38. The term array element electrode may be taken in what follows to refer both to the electrode 38 associated with a particular array element, and also to the node of an electrical circuit directly connected to this element electrode 38. The reference electrode 28 is also disposed upon the lower substrate 72 to realize an in-plane reference electrode geometry.

Figure 4:
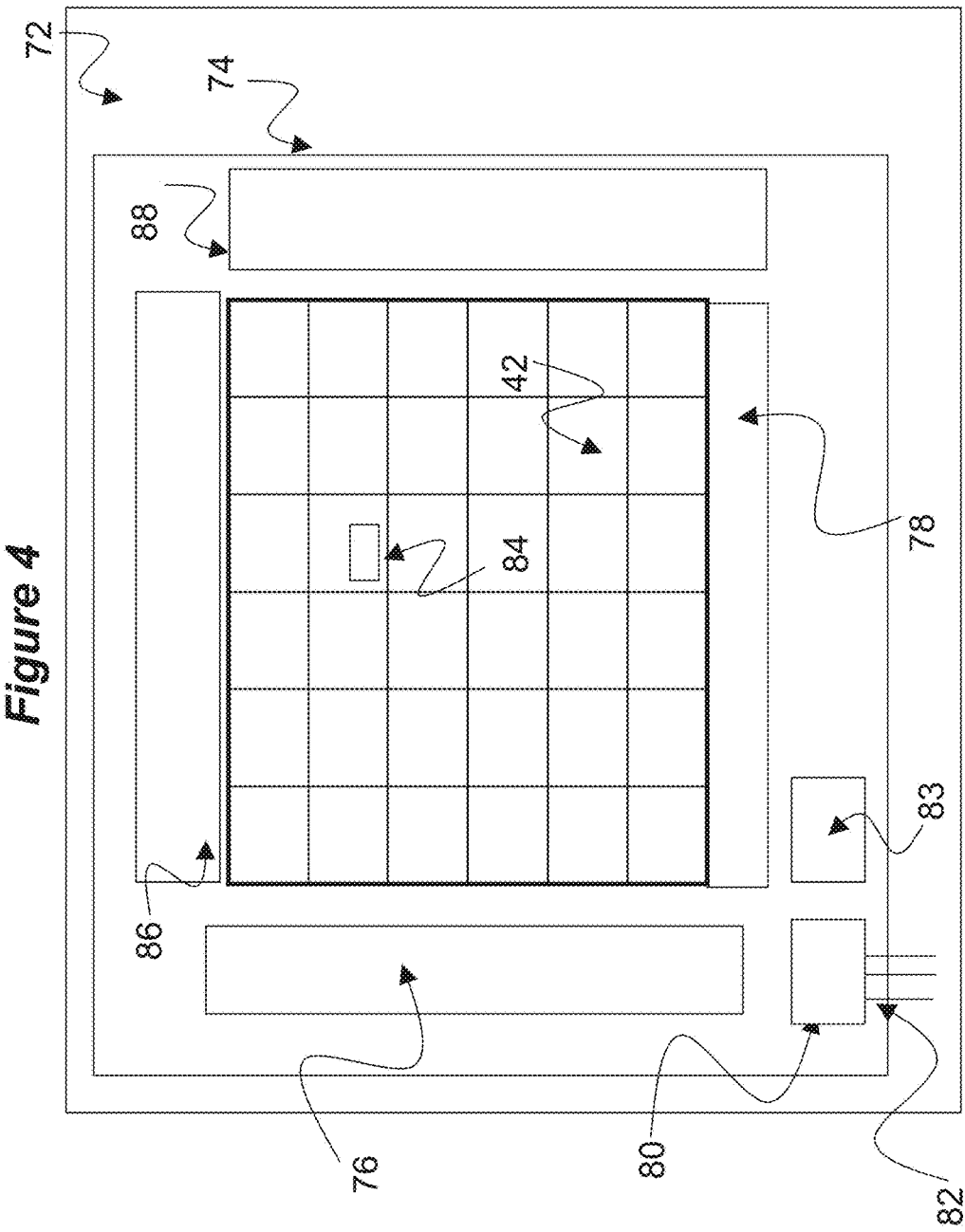
FIG. 4 is a schematic diagram depicting the arrangement of thin film electronics in the exemplary AM-EWOD device of FIG. 2 according to a first embodiment of the invention.

FIG. 4 is a schematic diagram depicting an exemplary arrangement of thin film electronics 74 upon the lower substrate 72. Each element of the electrode array 42 contains an array element circuit 84 for controlling the electrode potential of a corresponding element electrode 38. Integrated row driver 76 and column driver 78 circuits are also implemented in thin film electronics 74 to supply control signals to the array element circuits 84.

A serial interface 80 may also be provided to process a serial input data stream and write the required voltages to the electrode array 42. A voltage supply interface 83 provides the corresponding supply voltages, top substrate drive voltages, and other requisite voltage inputs as further described herein. The number of connecting wires 82 between the lower substrate 72 and external drive electronics, power supplies etc. can be made relatively few, even for large array sizes. Optionally the serial data input may be partially parallelized. For example if two data input lines are used, the first may supply data for columns 1 to X/2 and the second for columns (1+X/2) to M with minor modifications to the column driver 78 circuit. In this way the rate at which data can be written to the array is increased, which is a standard technique used in Liquid Crystal Display driving circuitry.

Generally, an exemplary AM-EWOD device that includes thin film electronics 74 is configured as follows. The AM-EWOD device includes a reference electrode 28 (e.g., an in-plane reference electrode 28) and a plurality of array elements, each array element including an array element electrode (e.g., array element electrodes 38).

Figure 5:
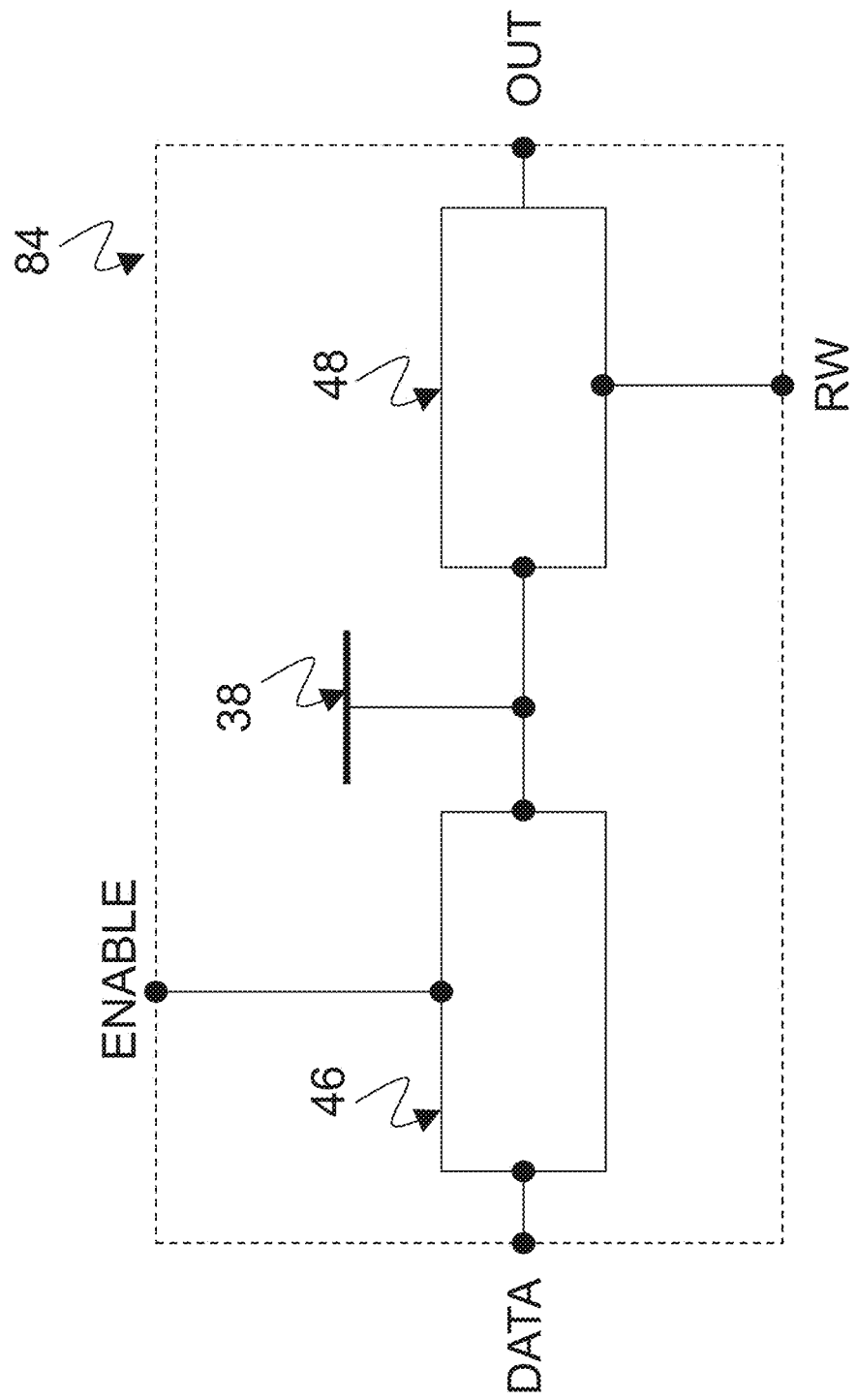
FIG. 5 is a schematic diagram depicting the array element circuit for use in the array elements of the exemplary AM-EWOD device of FIG. 2 according to a first embodiment of the invention.

Relatedly, the AM-EWOD device is configured to perform a method of controlling an actuation voltage to be applied to a plurality of array elements, including the AM-EWOD reference electrode 28 and a plurality of array elements, each array element including an array element electrode 38. The actuation voltage at each array element is defined by a potential difference between the array element electrode 38 and the reference electrode 28. The method of controlling the actuation voltage includes the steps of writing a voltage to at least a portion of the array element electrodes, and supplying a voltage signal to the reference electrode 28. FIG. 5 is a schematic diagram showing an example arrangement of thin film electronics 74 in the array element circuit 84. The array element circuit 84 contains an actuator circuit 46 which may typically perform the functions of:

(i) Writing data to a memory element contained within the actuator circuit and storing the data. The data to be written is typically input by means of an addressing line DATA which may be common to all elements within the same column of the array. The writing of data may typically be controlled by an addressing line ENABLE, which may typically be common to all elements within the same row of the array.

(ii) Writing a voltage signal to the array element electrode 38.

Examples of actuator circuits 46 may be found in U.S. Pat. No. 8,173,000 and UK applications GB1500260.3 and GB1500261.1 which may be considered as being incorporated by reference.

The array element circuit of FIG. 5 also contains a sensor circuit 48, which may be coupled by some means to the array element electrode 38. The sensor circuit 48 may be configured to sense some physical property of the array element electrode 38 or of a liquid droplet 4 in proximity to the array element electrode. Examples of quantities that may be sensed by the sensor circuit 48 include electrical impedance (e.g. capacitance) or temperature. The sensor circuit 48 may typically be addressed by one or more addressing signals, e.g. RW, which may be common to each element in the same row of the array and which are generated by sensor row addressing circuitry 88, realized in the thin film electronics and as shown in FIG. 4. The sensor circuit 48 will typically have at least one output OUT, which may for example be common to each array element in the same column of the array. The readout of sensor signal generated at OUT maybe performed, for example by a column detection circuit 86 which may also be realized in thin film electronics 74. Examples of sensor circuits may be found in U.S. Pat. No. 8,653,832 (impedance sensor) and in UK application GB1500261.1 which are incorporated by reference.

The remainder of the AM-EWOD device is of the standard construction previously described with respect to FIGS. 2-4 and may include a top substrate 36, a spacer 32 and a non-polar fluid 34 (e.g. an oil) as a surrounding medium within which the liquid droplets 4 are contained.

In operation the AM-EWOD device is configured to perform a droplet operation in accordance with the sequence by which the element electrodes are activated. Typical droplet operations, described in detail in the prior art references, include:

Moving droplets (from one array element to another),
Mixing droplets together (by merging and agitation),
Splitting droplets into two halves,
Dispensing of a small droplet from a large reservoir droplet, and
Inputting droplets onto the array from large input reservoirs, which may interface the device with the outside world.

The latter three operations involve the division of droplets into multiple smaller droplets. According to these operations, the volumes of the droplets produced may be defined, but are only controllable to within a certain precision which may be experimentally determined. Operationally these operations may be controlled using sensor feedback (as described in prior art references), but there is still some amount of variation in the sizes of the droplets created.

According to this embodiment, the AM-EWOD device of a first embodiment of the invention is configured to perform the step of diluting a "parent" droplet with a "diluent" droplet. The parent droplet may be comprised of any liquid, for example, sample, reagent or a reaction product from a previous reaction step. The parent droplet comprises a concentration of one or more species to be diluted. This species may comprise, for example, a quantity of chemical species, a solute, a molecule or bio-molecule, a particle or a cell.

The diluent droplet may be comprised of any liquid, for example, water or a buffer solution. Optionally, and preferably, the parent and diluent droplets may also contain a quantity of surfactant to aid manipulation of the droplets by electro-wetting.

In general, therefore, an aspect of the invention is a method of performing dilution of a droplet in an electrowetting on dielectric (EWOD) device. In exemplary embodiments, the dilution method includes the steps of: providing a parent droplet on a first portion of an electrode array of the EWOD device, wherein the parent droplet has a first concentration of a species; providing a diluent droplet on a second portion of the electrode array of the EWOD device; controlling actuation voltages applied to the electrode array of the EWOD device to join the parent droplet and the diluent droplet into a product droplet having a second concentration of the species different from the first concentration of the species in the parent droplet; controlling the actuation voltages applied to the electrode array to split the product droplet into one or more daughter droplets, the one or more daughter droplets having the second concentration of the species; and calibrating a dilution ratio, wherein the dilution ratio is based on a ratio of the second concentration of the species in the product droplet to the first concentration of the species in the parent droplet, by measuring a volume of the parent droplet and a volume of the diluent droplet.

Figure 6:
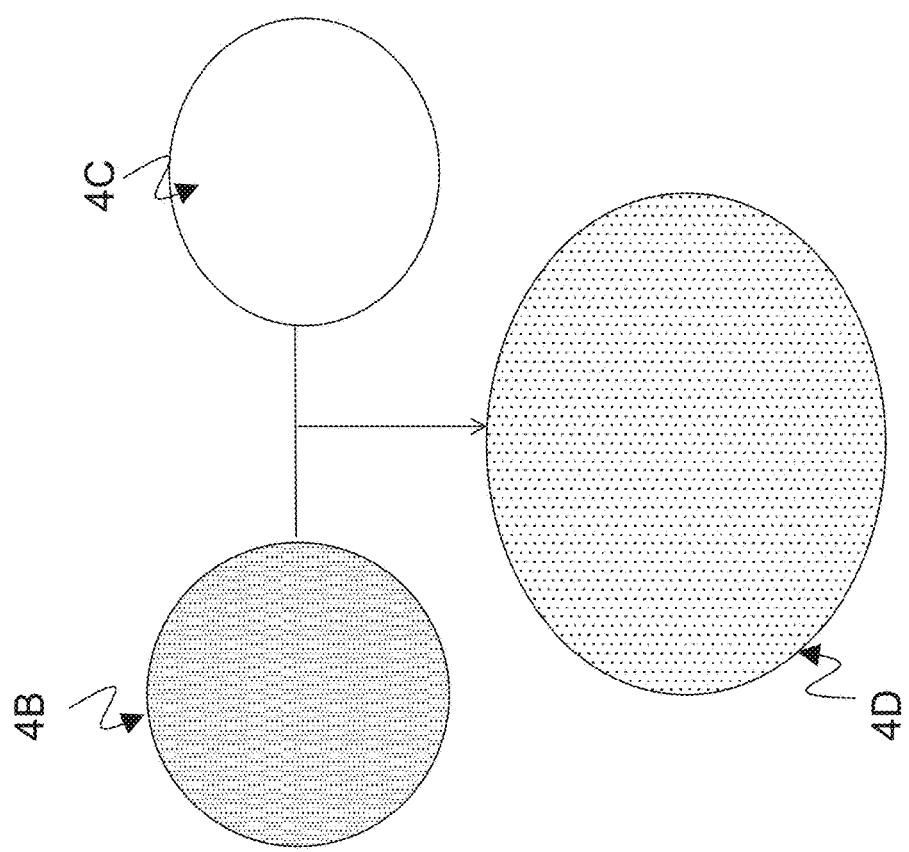
FIG. 6 shows a droplet manipulation protocol in accordance with a first embodiment of the invention.

FIG. 6 is illustrative of such a dilution method. The droplets participating in the dilution operation are designated as follows:

A parent droplet 4B, having a starting or first concentration of the species to be diluted of $C_B$.
A diluent droplet 4C, having a different starting concentration of the species to be diluted of $C_C$ (and where typically $C_C=0$).

The dilution method according to this embodiment is shown in FIG. 6 and is described as follows:

The volumes of both the parent and diluent droplets are measured, $V_B$ and $V_C$ respectively.
Droplets 4B and 4C are mixed together on the device to create a product droplet 4D, having a second (typically diluted) concentration of the species different from the first concentration in the parent droplet.
The concentration of the product droplet $C_D$ is determined from the measured volumes and known concentrations of both the parent and diluent droplets according to the formula:

$$C_D = \frac{V_C C_C + V_B C_B}{V_B + V_C} \quad \text{(equation 1)}$$

The dilution ratio $\beta$, i.e. the ratio by which the concentration of the species in the parent droplet has been diluted, or a ratio of the second concentration of the species in the product droplet to the first concentration of the species in the parent droplet, is therefore given by:

$$\frac{1}{\beta} = \frac{C_D}{C_B} = \frac{V_C C_C + V_B C_B}{(V_C + V_B) C_B} \quad \text{(equation 2)}$$

Optionally, and preferably, droplet volumes are measured using the integrated sensor capability of the device, although it will be appreciated that other methods of measuring droplet volumes may alternatively be employed (e.g. optical). In this manner, the dilution ratio may be calibrated based on measuring the volumes of the parent droplet and the diluent droplet.

An advantage of the first embodiment is that by measuring the volumes of both the parent and diluent droplets and by using this information to calculate the dilution ratio $\beta$, the value of $\beta$ may be measured very accurately. In the case where the measurement of the droplet volumes is performed by using an integrated capacitance sensor function, the volumes may be measured very accurately, typically to errors of one percent or less. In general this accuracy of volume measurement is higher or much higher than the precision to which the starting volumes of the dispensed droplets can be created (which may be typically on order 2-3%).

A further advantage of this embodiment is that by measuring $\beta$ very accurately, the known value of $\beta$ may be used to calculate the result of the assay to a high level of accuracy. Consider for example an assay whereby the aim is to measure the concentration Q of a material. According to the protocol of performing the assay on device, the input sample may be inputted as a parent droplet to the EWOD device, and first be diluted by the above methods by a target factor F, and the concentration $Q_2$ measured in the diluted sample or daughter droplet on device, for example by means of optical read-out (e.g. by absorbance change, optical fluorescence, or the like). According to conventional methods, the starting concentration Q would be calculated as $Q=Q_2 \times F$. According to the method of this invention, the actual dilution ratio $\beta$ achieved in each particular case is measured or determined by measuring the volumes of the parent and diluent droplets, and may be substituted for the target value F, and so the starting concentration may be much more accurately calculated based on the diluted concentration and dilution ratio as $Q=Q_2 \times \beta$.

A further advantage of this embodiment is that it is possible to define a target range of acceptable values for $\beta$. For example, in a given assay a target value $F=10$ with a tolerance of 1% may be defined. In this case $\beta$ may be measured for the dilution step and only if $0.99 \leq \beta \leq 1.01$ is the dilution step deemed to have been sufficiently accurate and the test allowed to proceed. Otherwise, for example, the dilution step may be repeated using new parent and diluent droplets until an acceptable value of $\beta$ is achieved.

According to a variant of the first embodiment, the volume of the product droplet $V_D$ may also be measured, for example as a check that the volume measurements of the parent ($V_B$) and diluent droplets ($V_C$) were performed correctly. For example, the conservation of liquid requires $V_D = V_B + V_D$, and so if this is found not be the case (to within a certain defined tolerance) an error condition may be reported and the dilution step repeated.

Figure 7:
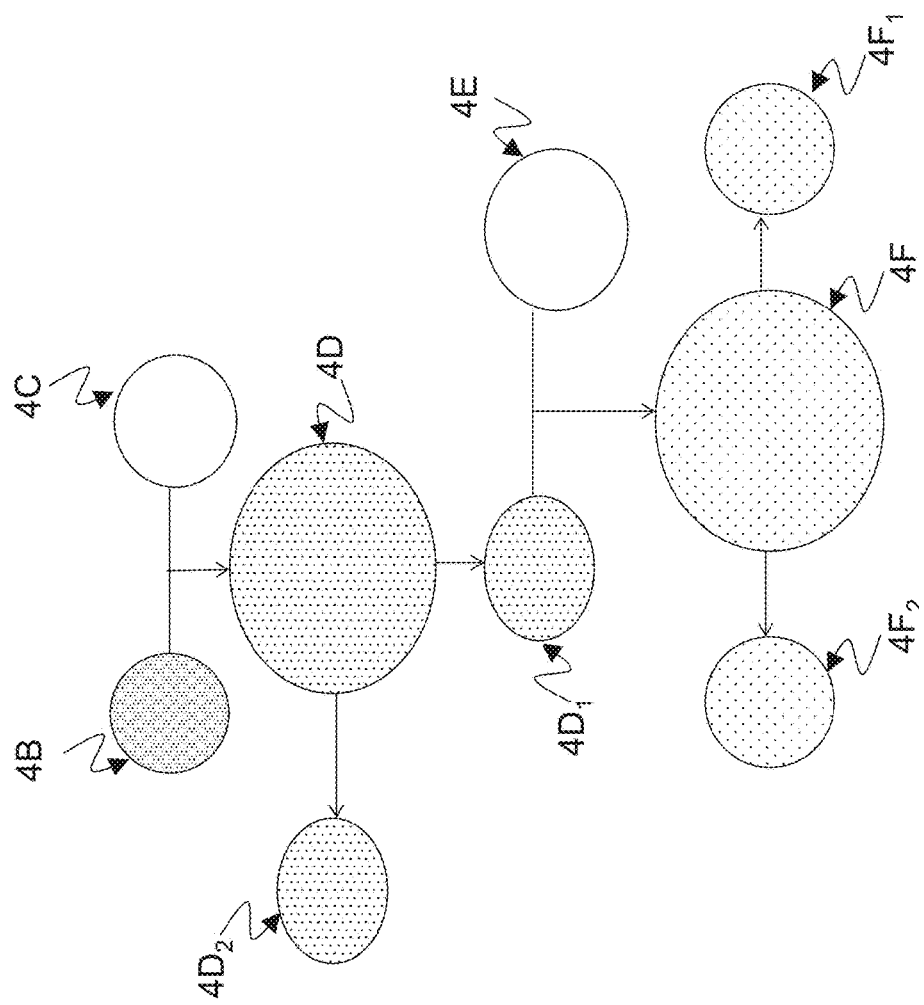
FIG. 7 shows a droplet manipulation protocol in accordance with a second embodiment of the invention.

A second embodiment of the invention is an extension of the first embodiment, whereby the dilution method of the first embodiment is used to perform a serial dilution curve, shown schematically in FIG. 7. In exemplary embodiments, a serial dilution may include the steps of serially repeating any embodiments of the described dilution methods, wherein a daughter droplet of a dilution step is the parent droplet in a next dilution step, and calibrating dilution ratios by measuring the volumes of the parent and diluent droplets participating in each dilution step.

FIG. 7 is illustrative of such a serial dilution method. Serial dilution is performed as follows:

Parent droplet 4B is diluted with diluent droplet 4C to create a product droplet 4D with a dilution ratio $\beta_1$, using the methods previously described.

Product droplet 4D is split into two components, $4D_1$ and $4D_2$, the volumes of which are measured, for example using the integrated sensor capability.

Droplet $4D_2$, having a measured concentration of the target species, constitutes a reaction droplet and is used to participate in an assay reaction (not shown).

Droplet $4D_1$ is further diluted with droplet 4E according to a second dilution step to produce a second generation product droplet 4F. The dilution ratio of the second dilution step $\beta_2$ is calculated using the same methods as previously described and from the measured volumes of participating droplets $4D_1$ and 4E. The overall dilution factor of droplet 4F is therefore equal to $\beta_1 \beta_2$, or more generally a product of dilution ratios at each dilution step.

Product droplet 4F is split into two components, $4F_1$ and $4F_2$, the volumes of which are measured, for example using the integrated sensor capability.

Droplet $4F_2$, having a measured concentration of the target species, constitutes a reaction droplet and is used to participate in an assay reaction (not shown).

Droplet 4F1 may optionally be further diluted in an arbitrary number of subsequent dilution steps such that a library of reaction droplets may be produced, each having a measured concentration of the species of interest according to the measured dilution factors.

The dilution factor $\beta$ at each dilution step may be any number>1, but may typically be in the range 2-10. The dilution factor $\beta$ at each dilution step may be the same, or may be different according to the requirements of the assay.

Figure 8:
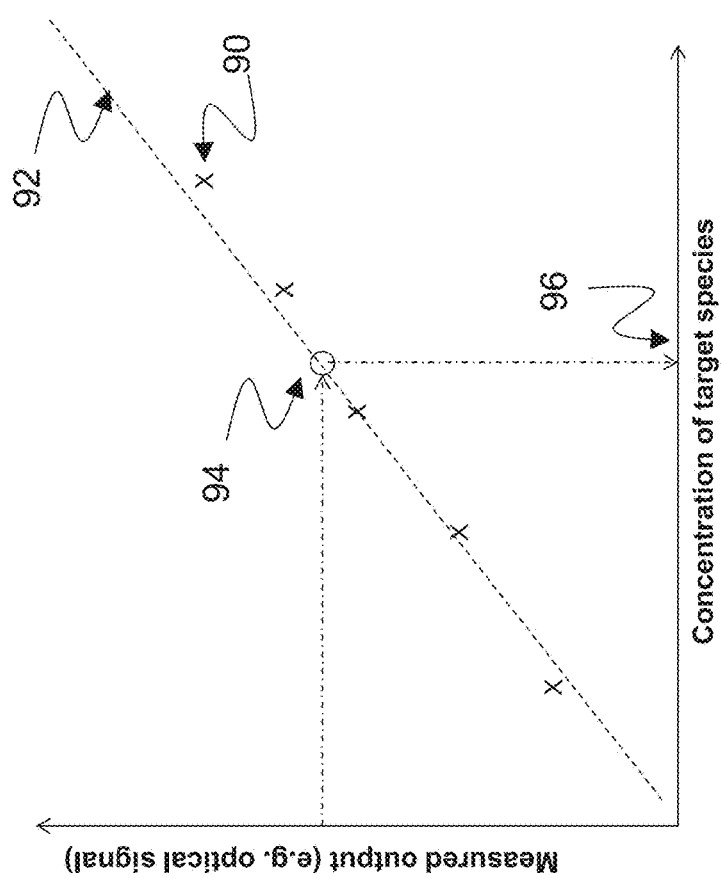
FIG. 8 is a pictorial representation of a standard curve in accordance with a second embodiment of the invention.

According to an example application of this embodiment, the reaction droplets may be further arranged to perform assay reactions with calibration to a standard curve, as illustrated in FIG. 8. This figure shows the concentration of target species plotted on the X-axis and the measured output of the assay (for example an optical signal) plotted on the Y-axis. In an exemplary implementation the following may be measured:

1. The output signal measured from a reference sample at different concentrations (reference data points 90 shown as an "x" in FIG. 8).
2. The output signal measured from the sample under test. The results from 1 may be used to construct a standard curve 92, derived for example by a linear fit to the measured data at each concentration of target species. The concentrations for each data point x are calculated using the basic method of the invention. The measured output from the sample droplet is then fit to the standard curve (sample data point 94 shown as an "o" in FIG. 8) to derive the concentration of the target species in this droplet.

An advantage is that by employing the methods of the invention, the x ordinate of the reference data points 90 may be determined very accurately, and more accurately than would be the case if the methods of the invention were not to be employed. This in turns results in a more acutely defined standard curve 92 and therefore the concentration of the target species 96 may ultimately be measured more accurately than otherwise would be possible.

Optionally, the methods of this embodiment may be further extended such that the sample is also serially diluted employing the methods of the invention, such that one or more sample data points may be generated, the sample data points having measured dilution factors, measured according to the basic methods of the invention. Such a method may be advantageous in further increasing the accuracy of the measurement of the concentration of the target species in the sample.

A third embodiment of the invention is similar to previous embodiments, whereby the individual droplet manipulations are configured to occur in such a way so that the species containing parent droplet remains stationary in one position on the array and the other participating droplets are merged into, or split out from, this position. In exemplary embodiments, the dilution method may include the steps of maintaining the parent droplet at one position on the electrode array; merging the diluent droplet into the parent droplet at the one position to form the product droplet; and splitting the daughter droplet from the product droplet at the one position to another different position on the electrode array.

Figure 9:
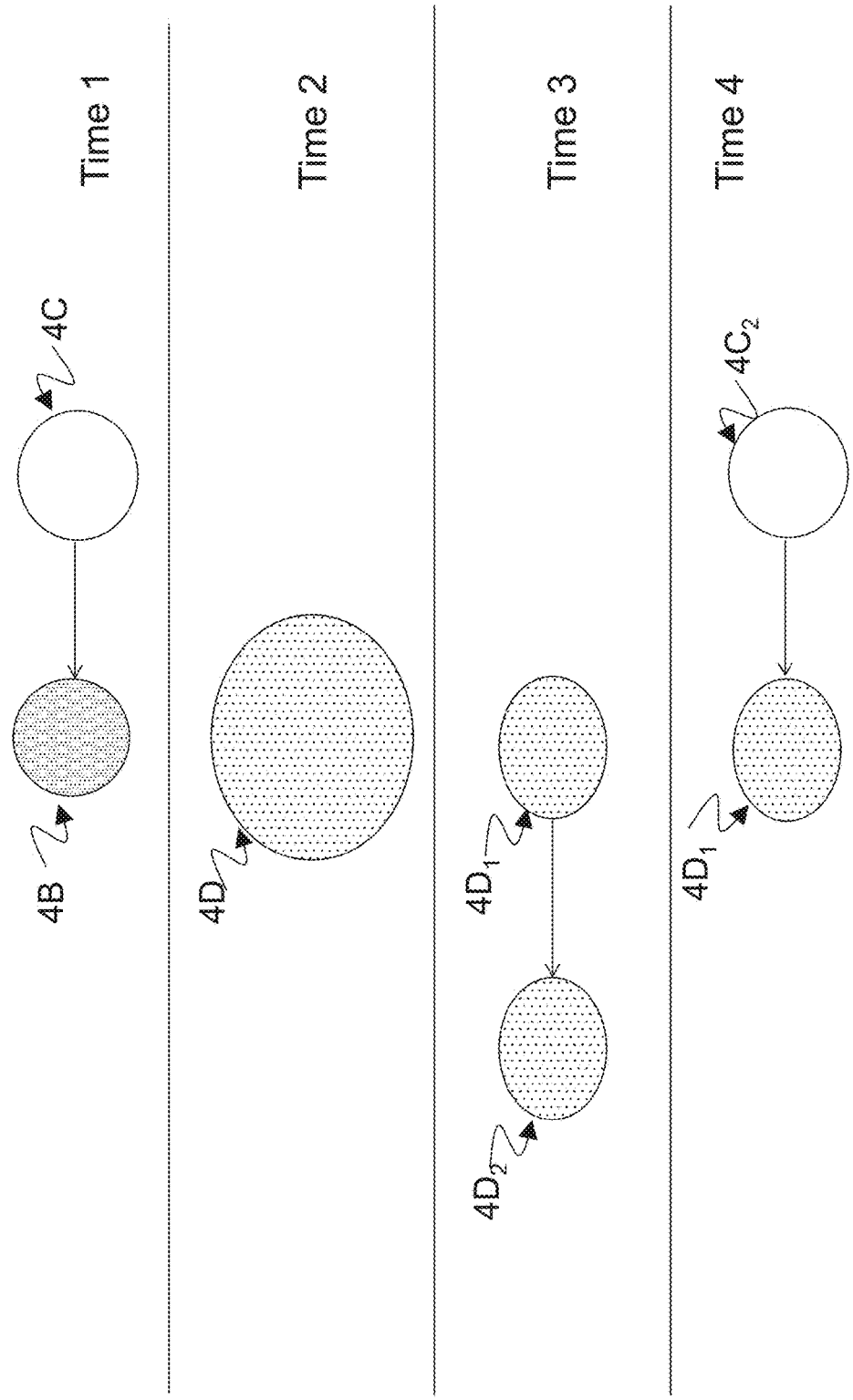
FIG. 9 shows a droplet manipulation protocol in accordance with a third embodiment of the invention.

An example implementation is shown in FIG. 9 where the arrows represent the movement of liquid. At time 1, the diluent droplet 40 is moved to the location of the parent droplet 4B, and at time 2 the droplets are mixed to create droplet 4D. At time 3, droplet 4D is split into components $4D_1$ and $4D_2$ by dispensing droplet $4D_2$ from the location of droplet 4D such that $4D_1$ is created in substantially the same position as previously occupied by droplet 4D. If further dilution stages are required, the same operation may be repeated, commencing, for example, by moving diluent droplet $4C_2$ to the location of droplet $4D_1$ at time 4.

An advantage of the third embodiment is that the method of serial dilution is implemented without having to move the parent droplet from its original location. This may be advantageous for one or more of the following reasons:

Such an arrangement minimizes the total area on chip required for the serial dilution step. This is advantageous for making efficient use of the device area and may reduce the overall size of the array required, therefore reducing cost. The value of such an efficiency saving is especially appreciable for assay protocols involving a number of dilution steps (e.g. a dilution series) or where multiple dilutions occur simultaneously on different parent droplets in different parts of the array.

In the case where the species of interest being diluted is "sticky", i.e. it has a tendency to adsorb to one or both of the hydrophobic coatings, the method of this embodiment is advantageous because it minimizes the movement path of the species containing parent droplet. It may therefore minimize the loss of sample to the surface. This may be advantageous in order to:

Ensure highly accurate dilution factors (with little or no un-accounted for sample loss).

Minimize the area of chip that may be contaminated by sample loss. This may have the overall effect of further reducing the total size of array required to perform the assay.

Figure 10:
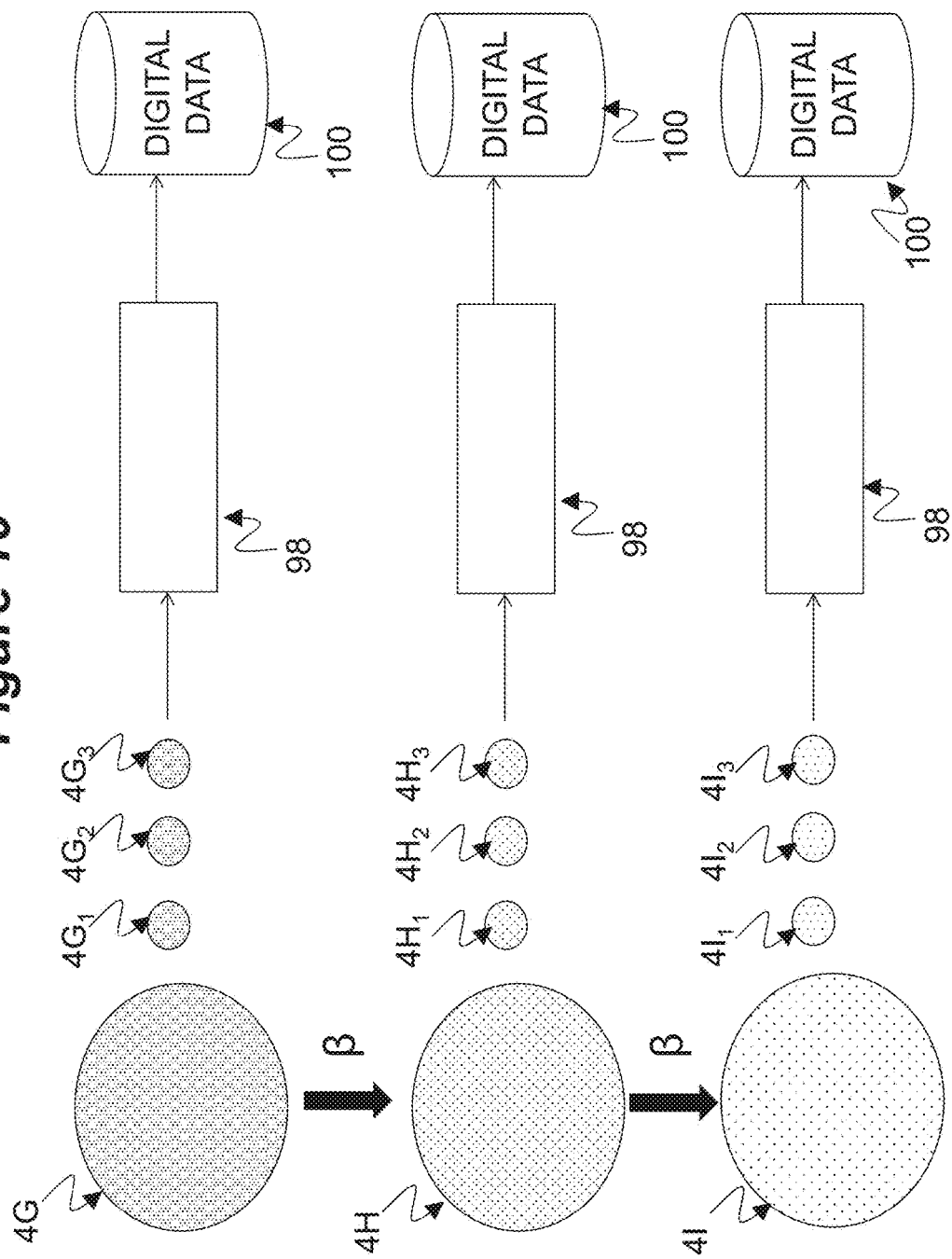
FIG. 10 shows a droplet manipulation protocol for performing a digital assay in accordance with a fourth embodiment of the invention.

A fourth embodiment of the invention is shown in FIG. 10. This embodiment utilizes the methods of any of the previous embodiments to perform a digital assay at a multiplicity of concentrations. In exemplary embodiments, therefore, the dilution method may include the steps of diluting a parent droplet into one or more daughter droplets of different concentrations in accordance with any of above embodiments, splitting the one or more daughter droplets into a plurality of smaller reaction droplets, and performing a digitized reaction with one of the reaction droplets.

Referring to FIG. 10, accordingly, some or all of the methods of embodiments 1 to 3 are used to prepare assay droplets 4G, 4H and 4I. Droplet 4H is created by the serial dilution of droplet 4G with an appropriate diluent droplet (not shown) such that the dilution ratio is $\beta$. Likewise, droplet 4I is created by the serial dilution of droplet 4H with an appropriate droplet of diluent (not shown) and a dilution ratio of $\beta$. Typically the target value of $\beta$ may be around 10, and the exact values of $\beta$ achieved are measured using the methods previously described.

The reaction droplet 4G is then used as a reservoir to create a number of smaller reaction droplets, for example $4G_1$, $4G_2$ and $4G_3$, by multiple dispensing operations. Likewise reaction droplets $4H_1$, $4H_2$ and 4H3 may be generated from droplet 4H, and reaction droplets $4I_1$, $4I_2$ and $4I_3$ may be created from droplet 4I.

The smaller reaction droplets (e.g. $4G_1$, $4G_2$, $4G_3$) may then be controlled so as to perform a digitized reaction 98, defined as a chemical reaction (which may involve further interactions with other droplets) and whose output is sensed as "0" or "1" in accordance with whether a measured property (for example an optical property) exceeds a certain threshold. Examples of such digitized reactions may include nucleic acid amplification reactions (e.g. Polymerase Chain Reaction (PCR), Recombinase Polymerase Amplification (RPA), immunoassay, an enzyme turnover assay, or any other example of a known assay.

The results of the assay are determined by measuring the digital output on multiple droplets (for example one hundred droplets) at each concentration. Depending on the concentration of the target species in the input sample, the optimum data for determining the concentration of the target species will be generated at the concentration of diluted droplets (e.g. 4G, 4H, 4I) where there is a probability of around 50% of the target molecule being present in the dispensed smaller droplets (e.g. $4G_1$). Accordingly, by performing the digital assay at multiple serial dilutions, it is possible to measure over a large range of input concentrations by performing the assay on a relatively small number of samples.

An advantage of this embodiment is that by accurately measuring the serial dilution ratios, the concentrations of droplets 4G, 4H and 4I are known accurately. It follows that the input concentration can be accurately determined from the analysis of the digital data 100 generated by the digital assays, since the concentration of the target species in the reacting droplets is accurately known.

The methods of this embodiment are particularly well suited to non-linear assays and to assays where it is desirable to measure the concentration of a target species in an input sample, where said concentration may vary over several order of magnitudes. Furthermore by employing serial dilution methods and performing the digital assay at multiple concentration ranges, it is possible to obtain an accurate quantitative answer by analysis of a much fewer number of droplets than would be required to be analyzed if no serial dilution was involved.

An aspect of the invention, therefore, is a method of performing dilution of a droplet in an electro-wetting on dielectric (EWOD) device. In exemplary embodiments, the dilution method includes the steps of: providing a parent droplet on a first portion of an electrode array of the EWOD device, wherein the parent droplet has a first concentration of a species; providing a diluent droplet on a second portion of the electrode array of the EWOD device; controlling actuation voltages applied to the electrode array of the EWOD device to join the parent droplet and the diluent droplet into a product droplet having a second concentration of the species different from the first concentration of the species in the parent droplet; controlling the actuation voltages applied to the electrode array to split the product droplet into one or more daughter droplets, the one or more daughter droplets having the second concentration of the species; and calibrating a dilution ratio, wherein the dilution ratio is based on a ratio of the second concentration of the species in the product droplet to the first concentration of the species in the parent droplet, by measuring a volume of the parent droplet and a volume of the diluent droplet. The dilution method may include any of the following features, either individually or in combination.

In an exemplary embodiment of the dilution method, a concentration of the species in the diluent droplet is zero.

In an exemplary embodiment of the dilution method, the diluent droplet is one of water or a buffer solution, and/or includes a surfactant.

In an exemplary embodiment of the dilution method, the species is at least one of a chemical species, a solute, a molecule or bio-molecule, a particle, or a cell.

In an exemplary embodiment of the dilution method, the EWOD device includes a sensor, and the dilution method further comprises measuring the volumes of the parent and diluent droplets with the sensor.

In an exemplary embodiment of the dilution method, the sensor is an integrated sensor that is integrated into array element circuitry of the EWOD device.

In an exemplary embodiment of the dilution method, the integrated sensor is an integrated capacitance sensor.

In an exemplary embodiment of the dilution method, the sensor is an optical sensor.

In an exemplary embodiment of the dilution method, the dilution ratio is between 2 and 10.

In an exemplary embodiment of the dilution method, the dilution method further includes the steps of: measuring volumes of each of the parent droplet and the diluent droplet; measuring a volume of the product droplet; and outputting an error condition when the volume of the product droplet does not equal a sum of the volumes of the parent droplet and the diluent droplet.

In an exemplary embodiment of the dilution method, the dilution method further includes the steps of: maintaining the parent droplet at one position on the electrode array; merging the diluent droplet into the parent droplet at the one position to form the product droplet; and splitting the daughter droplet from the product droplet at the one position to another different position on the electrode array.

In an exemplary embodiment of the dilution method, the method includes the steps of: performing serial dilution steps by serially repeating the dilution method of any of the embodiments, wherein a daughter droplet of a dilution step is the parent droplet in a next dilution step; and calibrating dilution ratios by measuring the volumes of the parent and diluent droplets participating in each dilution step.

In an exemplary embodiment of the dilution method, an overall dilution factor is a product of the dilution ratios at each dilution step.

In an exemplary embodiment of the dilution method, the dilution ratios are different at each dilution step.

In an exemplary embodiment of the dilution method, the dilution ratios are the same at each dilution step.

In an exemplary embodiment of the dilution method, each serial dilution step produces a reagent droplet, wherein the reagent droplets comprise a multiplicity of droplets of different concentrations.

In an exemplary embodiment of the dilution method, a dilution ratio factor of the multiplicity of droplets at each serial dilution step is one of a factor of two or a factor of ten.

Another aspect of the invention is a method of performing a digital assay. In exemplary embodiments, the digital assay method includes the steps of: diluting a parent droplet into one or more daughter droplets of different concentrations in accordance with the dilution method of any of the embodiments; splitting the one or more daughter droplets into a plurality of smaller reaction droplets; and performing a digitized reaction with at least one of the reaction droplets.

In an exemplary embodiment of the digital assay method, the digitized reaction of one of a nucleic acid amplification reaction, an immunoassay, or an enzyme turnover assay.

Another aspect of the invention is a method of measuring a concentration of species in a sample. In exemplary embodiments, the measuring method includes the steps of: inputting the sample as a parent droplet to an EWOD device, the sample having a starting concentration of the species; diluting the sample in accordance with the dilution method of any of the embodiments; determining the dilution ratio by measuring the volumes of the parent and diluent droplets; measuring a second concentration of the species in the daughter droplet; and calculating the starting concentration of the species based on the second concentration and the dilution ratio.

Although the invention has been shown and described with respect to a certain embodiment or embodiments, equivalent alterations and modifications may occur to others skilled in the art upon the reading and understanding of this specification and the annexed drawings. In particular, with regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

INDUSTRIAL APPLICABILITY

The described embodiments could be used to provide an enhance AM-EWOD device. The AM-EWOD device could form a part of a lab-on-a-chip system. Such devices could be used in manipulating, reacting and sensing chemical, biochemical or physiological materials. Applications include healthcare diagnostic testing, material testing, chemical or biochemical material synthesis, proteomics, tools for research in life sciences and forensic science.

What is claimed is:

1. A method of performing dilution of a droplet in an electro-wetting on dielectric (EWOD) device comprising the steps of:
providing a parent droplet on a first portion of an electrode array of the EWOD device, wherein the parent droplet has a first concentration of a species;
providing a diluent droplet on a second portion of the electrode array of the EWOD device;
controlling actuation voltages applied to the electrode array of the EWOD device to join the parent droplet and the diluent droplet into a product droplet having a second concentration of the species different from the first concentration of the species in the parent droplet;
calibrating a dilution ratio, wherein the dilution ratio is based on a ratio of the second concentration of the species in the product droplet to the first concentration of the species in the parent droplet, by measuring a volume of the parent droplet and a volume of the diluent droplet.

2. The dilution method of claim 1, wherein a concentration of the species in the diluent droplet is smaller than the concentration of the species in the parent droplet by a factor of one of 2, 10, 1000, or 1,000,000, or where the concentration of the species in the diluent droplet is zero.

3. The dilution method of claim 1, wherein the diluent droplet is one of water or a buffer solution, and/or includes a surfactant.

4. The dilution method of claim 1, wherein the species is at least one of a chemical species, a solute, a molecule or bio-molecule, a particle, or a cell.

5. The dilution method of claim 1, wherein the EWOD device includes a sensor, and the dilution method further comprises measuring the volumes of the parent and diluent droplets with the sensor.

6. The dilution method of claim 5, wherein the sensor is an integrated sensor that is integrated into array element circuitry of the EWOD device.

7. The dilution method of claim 6, wherein the integrated sensor is an integrated capacitance sensor.

8. The dilution method of claim 5, wherein the sensor is an optical sensor.

9. The dilution method of claim 1 comprising the further step of controlling the actuation voltages applied to the electrode array to split the product droplet into one or more daughter droplets, the one or more daughter droplets having the second concentration of the species.

10. The dilution method of claim 1, wherein the dilution ratio is between 2 and 10.

11. The dilution method of claim 1, further comprising:
measuring volumes of each of the parent droplet and the diluent droplet;
measuring a volume of the product droplet; and
outputting an error condition when the volume of the product droplet does not equal a sum of the volumes of the parent droplet and the diluent droplet.

12. The dilution method of claim 1, further comprising:
maintaining the parent droplet at one position on the electrode array;
merging the diluent droplet into the parent droplet at the one position to form the product droplet; and
splitting the daughter droplet from the product droplet at the one position to another different position on the electrode array.

13. The dilution method of claim 1, comprising:
performing serial dilution steps by serially repeating the method of claim 1, wherein a daughter droplet of a dilution step is the parent droplet in a next dilution step; and
calibrating dilution ratios by measuring the volumes of the parent and diluent droplets participating in each dilution step.

14. The dilution method of claim 13, wherein an overall dilution factor is a product of the dilution ratios at each dilution step.

15. The dilution method of claim 12, wherein the dilution ratios are different at each dilution step, or wherein the dilution ratios are the same at each dilution step.

16. The dilution method of claim 13 wherein each serial dilution step produces a reagent droplet, wherein the reagent droplets comprise a multiplicity of droplets of different concentrations.

17. The dilution method of claim 16, wherein the dilution factor of the multiplicity of droplets at each serial dilution step is one of a factor of two or a factor of ten.

18. A method of performing a digital assay comprising the steps of: diluting a parent droplet into one or more daughter droplets of different concentrations in accordance with the dilution method of claim 1;
splitting the one or more daughter droplets into a plurality of smaller reaction droplets;
performing a digitized reaction with at least one of the reaction droplets.

19. The method of claim 18, wherein the digitized reaction of one of a nucleic acid amplification reaction, an immunoassay, or an enzyme turnover assay.

20. A method of measuring a concentration of species in a sample comprising the steps of:
inputting the sample as a parent droplet to an EWOD device, the sample having a starting concentration of the species;
diluting the sample in accordance with the dilution method of claim 1;
determining the dilution ratio by measuring the volumes of the parent and diluent droplets;
measuring a second concentration of the species in the daughter droplet; and
calculating the starting concentration of the species based on the second concentration and the dilution ratio.

* * * * *